United States Patent
Yamamoto et al.

(10) Patent No.: US 8,580,057 B2
(45) Date of Patent: Nov. 12, 2013

(54) APPARATUS AND METHOD FOR ULTRASONIC PROCESSING OF A FIBROUS WEB

(75) Inventors: Hiroki Yamamoto, Kagawa (JP); Akihide Ninomiya, Kagawa (JP); Yoshihiko Matsumoto, Kagawa (JP)

(73) Assignee: Unicharm Corporation, Ehime (JP)

( * ) Notice: Subject to any disclaimer, the term of this patent is extended or adjusted under 35 U.S.C. 154(b) by 0 days.

(21) Appl. No.: 13/819,727

(22) PCT Filed: Sep. 27, 2011

(86) PCT No.: PCT/JP2011/005421
§ 371 (c)(1),
(2), (4) Date: Feb. 28, 2013

(87) PCT Pub. No.: WO2012/042842
PCT Pub. Date: Apr. 5, 2012

(65) Prior Publication Data
US 2013/0174965 A1   Jul. 11, 2013

(30) Foreign Application Priority Data
Sep. 30, 2010   (JP) ................................ 2010-223075

(51) Int. Cl.
*B32B 37/00* (2006.01)
(52) U.S. Cl.
USPC ........ 156/73.1; 156/290; 156/555; 156/580.1
(58) Field of Classification Search
USPC .......... 156/73.1, 290, 308.2, 308.4, 555, 580, 156/580.1, 580.2, 582
See application file for complete search history.

(56) References Cited

U.S. PATENT DOCUMENTS

| | | | |
|---|---|---|---|
| 6,537,401 B2* | 3/2003 | Couillard et al. | 156/64 |
| 7,887,656 B2* | 2/2011 | Yamamoto | 156/73.1 |
| 8,211,256 B2* | 7/2012 | Nakakado | 156/73.1 |
| 2005/0145317 A1 | 7/2005 | Yamamoto | |
| 2010/0096065 A1 | 4/2010 | Yamamoto | |
| 2010/0116409 A1 | 5/2010 | Yamamoto | |

FOREIGN PATENT DOCUMENTS

| | | |
|---|---|---|
| JP | 58-39836 | 3/1983 |
| JP | 10-513128 | 12/1998 |
| JP | 2004-298413 | 10/2004 |
| JP | 2010-099132 | 5/2010 |
| JP | 2010-115283 | 5/2010 |

OTHER PUBLICATIONS

International Search Report from corresponding PCT application No. PCT/JP2011/005421 dated Dec. 13, 2011 (1 pg).

* cited by examiner

*Primary Examiner* — James Sells
(74) *Attorney, Agent, or Firm* — Brinks Gilson & Lione

(57) ABSTRACT

An apparatus and a method for ultrasonic processing improved so as to prevent a fibrous web from being disfigured due to the ultrasonic processing. In an apparatus to ultrasonically process a fibrous web running in a machine direction MD, a first mechanical element defined by one of an ultrasonic horn and an anvil and a second mechanical element defined by the other of the ultrasonic horn and the anvil are moved forward or backward in a direction crossing the machine direction MD so as to pass transversely across the fibrous web.

20 Claims, 10 Drawing Sheets

APPARATUS AND METHOD FOR ULTRASONIC PROCESSING OF A FIBROUS WEB

RELATED APPLICATION

This application is a 35 U.S.C. §371 national phase filing of International Patent Application No. PCT/JP2011/005421, filed Sep. 27, 2011, through which and to which priority is claimed under 35 U.S.C. §119 to Japanese Patent Application No. 223075, filed Sep. 30, 2010.

TECHNICAL FIELD

The present disclosure relates to apparatuses and methods for ultrasonically processing a fibrous web continuously running in a machine direction.

BACKGROUND

There are known apparatuses adapted to make a nonwoven fabric containing thermoplastic synthetic fibers or a film of thermoplastic synthetic resin run in the form of a fibrous web in a machine direction and to process such a web ultrasonically in the course of running.

For example, the ultrasonic processing machine disclosed in JP 1983-39836U (PTL 1) includes a processing horn and a pressure roller adapted to cooperate with the processing horn. The processing horn and the pressure roller respectively rotate to apply ultrasonic waves to an object so that the object may be continuously sealed.

The rotating seal system disclosed in JP 1998-513128 A (PTL 2) includes a drum rotating in the direction in which an object in the form of a fibrous web is being processed, a first heat energy input means attached to the peripheral surface of the drum so as to extend in the cross direction in which the drum rotates and a second heat energy input means attached to the drum so as to rotate together with the drum and simultaneously to move in the cross direction. The object being processed is located between the first heat energy input means and the second heat energy input means. The second heat energy input means moves in the cross direction in combination with the first heat energy input means to inject heat energy into the object being processed during rotation of the drum and, upon completion of heat energy input, the second heat energy input means moves away from the first heat energy input means to its initial position. One of the first and second heat energy input means is an ultrasonic vibrating horn and the other is an anvil.

CITATION LIST

Patent Literature

{PTL 1} JP 1983-39836 U
{PTL 2} JP 1998-513128 A

SUMMARY

Technical Problem

In the machine disclosed in PTL 1, the ultrasonic processed region is formed on a fibrous web necessarily parallel to the machine direction and it is impossible for this machine to obtain an ultrasonic processed region extending in the cross direction.

In the rotating seal system disclosed in PTL 2, with regard to the object being processed which is running in the machine direction, it is possible to obtain an ultrasonic-sealed region extending in the cross direction. However, in this rotating seal system, the first heat energy input means is fixed to the drum. In addition, the object being processed is fixed to the first heat energy input means; in other words, kept unmovable with regard to the rotating drum when the object is subjected to the heat energy input. With the first heat energy input means used in this manner, small agglomerations of fused thermoplastic synthetic resin ingredients contained in the object being processed may adhere to the first heat energy input means; or eventually such small agglomerations grow to larger agglomerations in the course of being repetitively used. Whether such agglomerations are small or large, accumulation of such agglomerations between the first and second heat energy input means may prevent these means from uniformly injecting heat energy to the object being processed and thereby prevent the sealed region from being increased in strength and/or being improved in appearance.

An object of the present invention is to provide an improved apparatus and a method for ultrasonic processing to solve such problems.

Solution to Problem

According to the present invention, there are provided an apparatus as a first aspect of the present invention and a method as a second aspect of the present invention.

The first aspect of the present invention relates to the apparatus for repetitive ultrasonic processing of a fibrous web continuously running in a machine direction by first and second mechanical elements adapted to sandwich the fibrous web in its thickness direction. Whilst being sandwiched in this way, the first and second mechanical elements act to ultrasonically process the fibrous web, preferably by providing seal-regions.

The apparatus, according to the first aspect of the present invention, includes an upstream side conveying means and a downstream side conveying means adapted to run a fibrous web continuously in a machine direction. A drum is located between the upstream side conveying means and the downstream side conveying means, the drum having an outer peripheral surface adapted to continuously rotate in a counterclockwise direction RD at a circumferential velocity equal to a running velocity of the fibrous web and adapted to support the fibrous web placed thereon, the outer peripheral surface being formed with a plurality of ultrasonic processing spaces each being in communication with the inside and the outside of the drum. The first mechanical elements are each located inside the drum in one of the processing spaces so that the first mechanical element is adapted to repetitively move back-and-forth in a direction crossing the machine direction to pass transversely across the fibrous web. The second mechanical elements are each located outside the drum in one of the processing spaces and adapted so that the second mechanical element repetitively moves back-and-forth in synchronization with the back-and-forth movement of the first mechanical element in the same direction as the direction in which the first mechanical element moves back-and-forth. The first and second mechanical elements are adapted to cooperate with each other to subject the fibrous web lying in each of the processing spaces during one of the forward and backward movements to ultrasonic processing, and at least one of the first and second mechanical elements is adapted to be spaced from the fibrous web in order to stop the ultrasonic processing during the other of the forward and backward movements.

The second aspect of the present invention relates to the method for repetitive ultrasonic processing of a fibrous web continuously running in a machine direction by first and second mechanical elements adapted to sandwich the fibrous web in its thickness direction.

The method according to the second aspect of the present invention includes the steps of continuously feeding the fibrous web in the machine direction and placing the fibrous web on an outer peripheral surface of a drum continuously rotating in the counterclockwise direction RD at a circumferential velocity equal to a running velocity of the fibrous web; using the first mechanical elements, each located inside the drum in one of a plurality of ultrasonic processing spaces formed in the outer peripheral surface of the drum so as to be in communication with the inside and the outside of the drum, to repeat back-and-forth movement in a direction crossing the machine direction and to pass transversely across the fibrous web, and using the second mechanical elements each located outside the drum at one of the ultrasonic processing space to move back-and-forth in synchronization with the back-and-forth movement of the first mechanical elements in the same direction as the direction in which the first mechanical elements move back-and-forth; and arranging the first and second mechanical elements to cooperate with each other during either the forward movement or the backward movement to process the fibrous web lying in each of the processing spaces with the ultrasonic processing and spacing at least one of the first and second mechanical elements from the fibrous web during the other of the forward movement and the backward movement to stop the ultrasonic processing.

Advantageous Effects of Invention

According to one or more embodiments of the present invention, the first mechanical element, which may be defined by one of the ultrasonic horn and the anvil, and the second mechanical element, which may be defined by the other of the ultrasonic horn and the anvil, are moved forward in the direction crossing the machine direction so as to pass transversely across the fibrous web and thereby the fibrous web is subjected to the ultrasonic processing. Therefore, even if a small agglomerate of thermoplastic synthetic resin formed due to the ultrasonic processing adheres to the first and/or the second mechanical element, the fibrous web sliding on the first and the second mechanical elements functions to wipe off such small agglomerate. In consequence, such small agglomerate should not interfere with the ultrasonic processing.

DESCRIPTION OF EMBODIMENTS

Details of an ultrasonic processing apparatus according to the present invention will be more fully understood from the description given hereunder with reference to the accompanying drawings.

Figure 1:
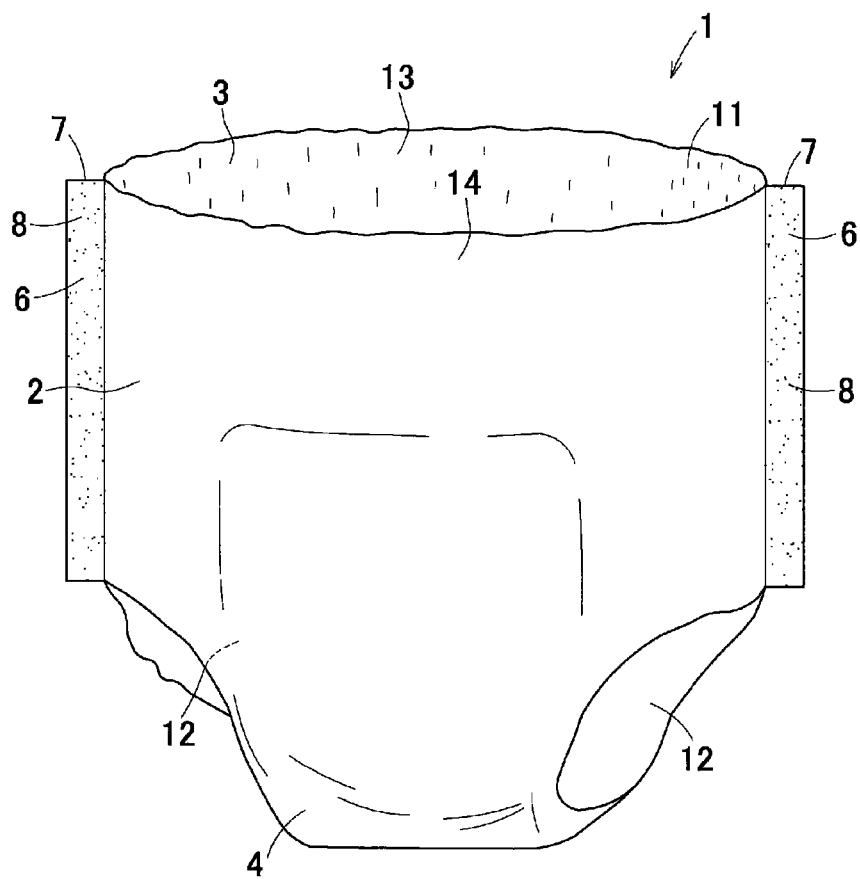
FIG. 1 A perspective view of a disposable diaper.

Referring to FIG. 1, this is a perspective view of one non-limiting example of a pants-type disposable diaper 1 obtained by use of an ultrasonic processing apparatus 50 to be hereinafter described. The diaper 1 includes a front waist region 2, a rear waist region 3 and a crotch region 4 wherein respective side edges 6, 7 of these front and rear waist regions 2, 3 are joined together along respective seal-regions 8 and thereupon the diaper 1 is formed with a waist-opening 11 and leg-openings 12. The waist-opening 11 and the leg-openings 12 are provided along respective peripheral edges thereof with elastics (not shown) attached under tension thereto so that the respective peripheral edges may be elastically contractible. In the front waist region 2, the rear waist region 3 and the crotch region 4, an inner sheet 13 adapted to come in contact with the wearer's skin is formed of a liquid-pervious nonwoven fabric made of thermoplastic synthetic fibers and an outer sheet 14 adapted to come in contact with a garment of the wearer is formed of a laminated sheet included of a liquid-impervious film made of a thermoplastic synthetic resin and a nonwoven fabric made of a thermoplastic synthetic resin and bonded to the outer surface of the film. The diaper 1 further includes an absorbent structure (not shown) itself of known art sandwiched between the inner sheet 13 and the outer sheet 14.

The seal-regions 8 in this diaper 1 are provided by laying the side edges 6 of the front waist region 2 on the side edges 7 of the rear waist region 3 to overlap each other and then processing these side edges by an ultrasonic processing apparatus to be hereinafter described. More specifically, the seal-regions 8 are provided by laying the inner and outer sheets 13, 14 defining the front waist region 2 on the inner and outer sheets 13, 14 defining the rear waist region 3 and then processing them by the ultrasonic processing apparatus 50.

Figure 2:
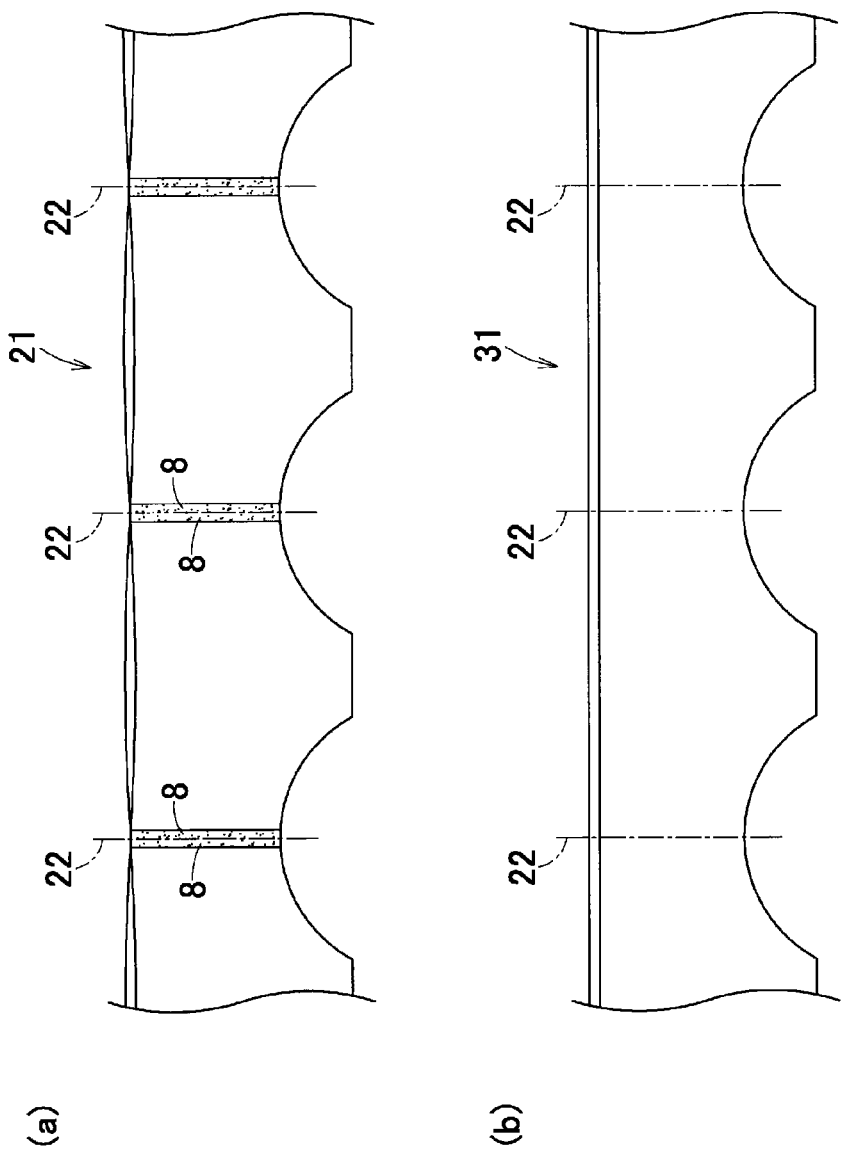
FIG. 2 (a) A diagram illustrating a web of contiguous diapers including the disposable diaper shown in FIG. 1. (b) A diagram illustrating a fibrous web from which the web of contiguous diapers is obtained.

Referring to FIG. 2(a), this is a partially cutaway perspective view showing a non-limiting web of contiguous diapers 21 including a plurality of the diapers 1 shown in FIG. 1 contiguously arranged in the transverse direction and, referring to FIG. 2(b), this shows a partially cutaway perspective view of the fibrous web 31 used to obtain the web of contiguous diapers 21.

In the web of contiguous diapers 21 shown in FIG. 2(a), a plurality of proposed cutting lines 22 are arranged at regular intervals in the longitudinal direction. On both sides of the respective proposed cutting lines 22, the seal-regions 8 as shown in FIG. 1 are provided in contiguous with each other. The diaper 1 can be obtained by cutting such web of contiguous diapers 21 along the respective proposed cutting lines 22. In the fibrous web 31 shown in FIG. 2(b), the proposed cutting lines 22 are shown as they are in FIG. 2(a) but the web of contiguous diapers 21 is in a state before the seal-regions 8 are formed. Such fibrous web 31 may be processed by the ultrasonic processing apparatus 50 to provide the seal-regions 8 and thereby to obtain the web of contiguous diapers 21 shown in FIG. 2(a). However, fibrous webs having alternative configurations may alternatively be processed by the apparatus of the present invention.

Figure 3:
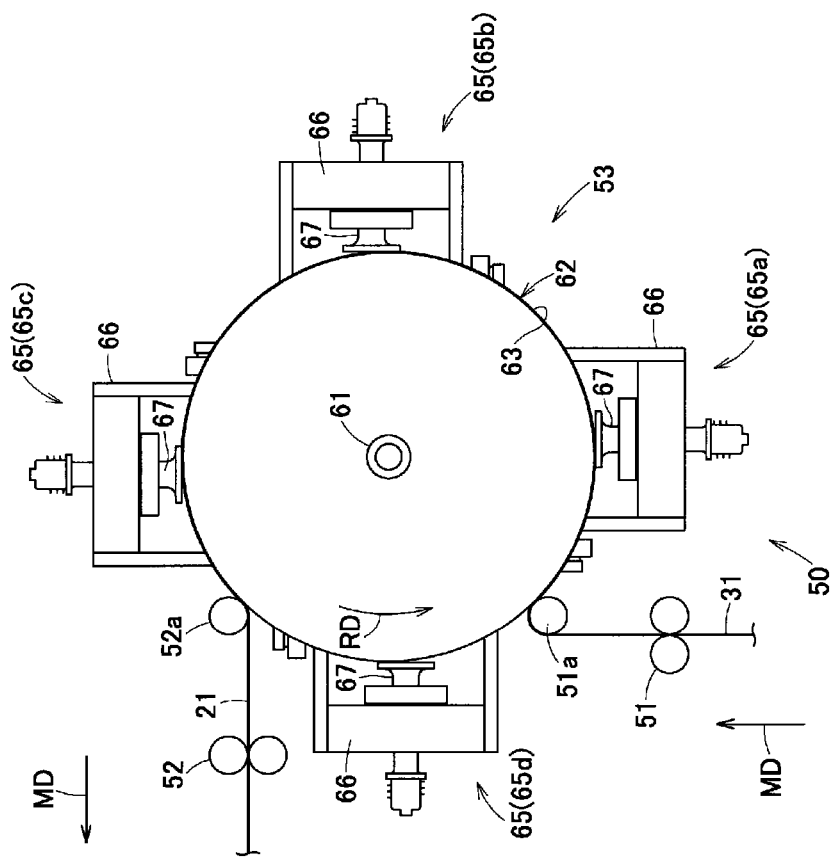
FIG. 3 An end view of an ultrasonic processing apparatus as viewed from one end of its rotary shaft.

Referring to FIG. 3, this is an end view of the ultrasonic processing apparatus 50 as viewed from one end of its rotary shaft 61. The ultrasonic processing apparatus 50 repetitively processes a fibrous web such as the fibrous web 31 illustrated in FIG. 2(b) to obtain the web of contiguous diapers 21 as illustrated in FIG. 2(a). In FIG. 3, a machine direction is denoted by MD and a rotational direction (counterclockwise direction) of a rotary drum 62 to be hereinafter described is denoted by RD. In a preferred embodiment, the ultrasonic processing apparatus 50 includes a pair of first guide rolls 51 located on an upstream side as viewed in the machine direction MD and serving as upstream conveying means, a pair of second guide rolls 52 located on a downstream side as viewed in the machine direction MD and serving as downstream conveying means and an ultrasonic processing station 53 located between the first and second guide rolls 51, 52. The fibrous web 31 continuously runs from the first guide rolls 51 toward the second guide rolls 52 and passes through the ultrasonic processing station 53 in the course of running in this manner.

In the following paragraphs 21 to 28, a detailed description is provided of one way of putting the invention into practice. The invention is not to be limited to the detail of the arrangement described since alternative arrangements are envisaged, utilizing the essential features claimed.

The ultrasonic processing apparatus 50 includes a drum 62 adapted to rotate together with the rotary shaft 61 in the direction RD and, in this example, four ultrasonic processing units 65 provided separately of the drum 62 and arranged at regular pitches or intervals in a circumferential direction of the drum 62 so that these ultrasonic processing units 65 may rotate in the direction RD together with the rotary shaft 61. In FIG. 3, these four preferred embodiments of ultrasonic processing units 65 are denoted by reference numerals 65a, 65b, 65c and 65d. The fibrous web 31, having passed through the first guide rolls 51, may be guided by a guide (or pinch) roll 51a and put in close contact with an outer peripheral surface 63 of the drum 62. In the ultrasonic processing station 53, a running velocity of the fibrous web 31 in the machine direction MD and a circumferential velocity of the outer peripheral surface 63 of the drum 62 are previously regulated to be equal to each other. The outer peripheral surface 63 is preferably directly surface-treated or coating-treated with a rubber sheet to prevent slippage of the fibrous web 31. The four ultrasonic processing units 65a through 65d generically named as the ultrasonic processing units 65 are uniform in the construction thereof. In FIG. 3, each of the exemplified, non-limiting, ultrasonic processing units 65 includes a carrier 66 and an ultrasonic horn 67.

Figure 4:
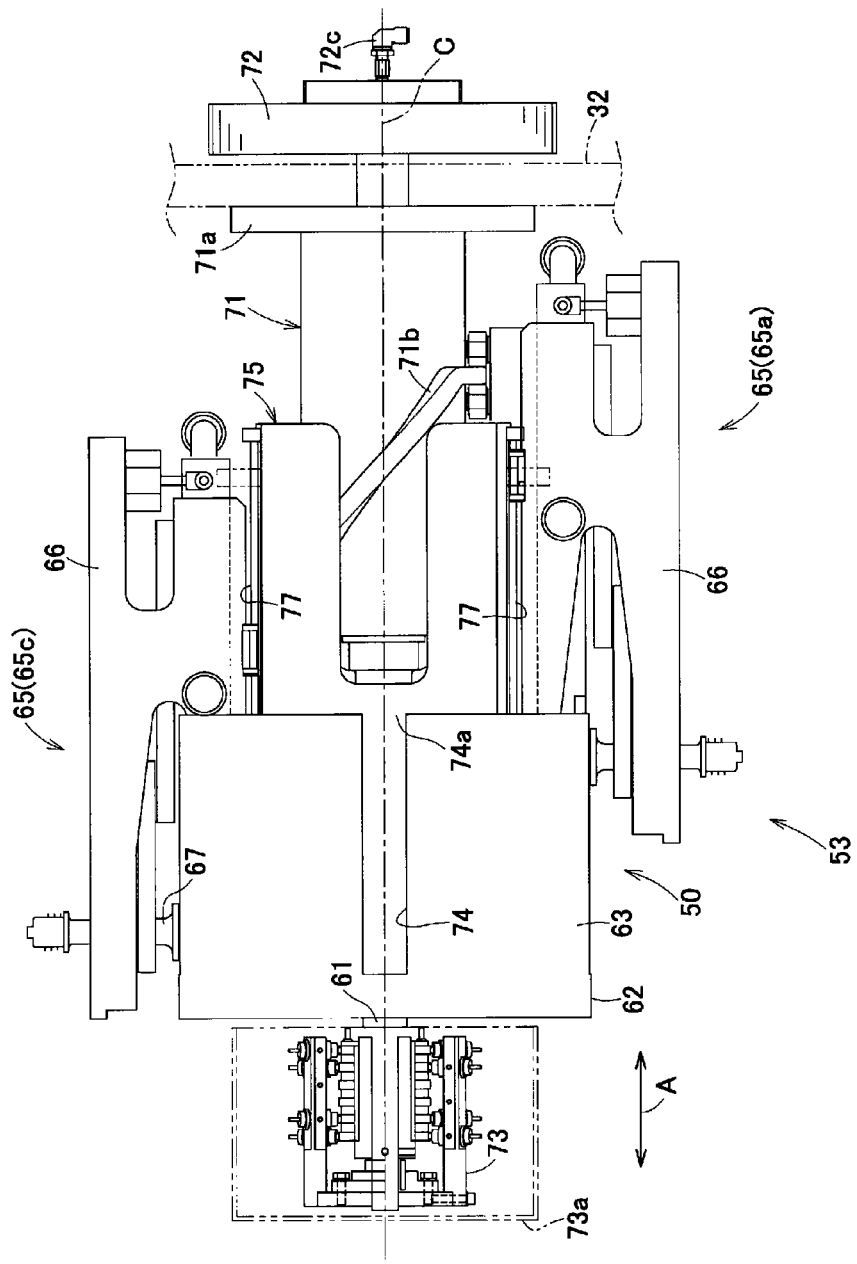
FIG. 4 A partially omitted side view of the ultrasonic processing apparatus shown in FIG. 3.

Referring to FIG. 4, this is a side view of the ultrasonic processing station 53 in FIG. 3 wherein the ultrasonic processing unit 65b and the fibrous web 31 are not illustrated. In FIG. 4, the ultrasonic processing apparatus 50 includes a stationary cylinder 71 having a flange 71a fixed to a wall 32 indicated by an imaginary line on the right hand side and the rotary shaft 61 horizontally extends through the stationary cylinder 71. The rotary shaft 61 is provided on one end thereof with a main input pulley 72 and on the other end thereof with an ultrasonic transmitting slip ring 73 housed within a protecting case 73a indicated by an imaginary line. The slip ring 73 and the case 73a are not shown in FIG. 3. The stationary cylinder 71 is provided on its peripheral surface with a rib-like cam 71b protruding from the peripheral surface. The rotary shaft 61 having a rotational center indicated by an imaginary line C is rotated as a main input belt (not shown) revolves on the main pulley 72. The rotary shaft 61 is provided, in addition to the drum 62, with a column 75 lying inside the drum 62 and fixed thereto so that the column 75 also may rotate together with the rotary shaft 61 in the direction RD. The column 75 is provided with the carriers 66 adapted for reciprocal movement in a direction indicated by a two-headed arrow A in parallel to the rotary shaft 61. Considering the reciprocating movement in the direction indicated by the two-headed arrow A in the ultrasonic processing station 53, the movement in a direction from the main pulley 72 toward the drum 62 is forward movement and the movement opposed to such movement is backward movement. The main pulley 72 is provided with a rotary connector 72c serving to supply air cylinders 83 (See FIG. 8) operatively associated with the respective ultrasonic processing units 65a through 65d with compressed air.

The outer peripheral surface 63 of the drum 62 is provided with elongate ultrasonic processing spaces 74 which are in communication with the inside and the outside of the drum 62. Each of the processing spaces 74 extends in parallel to the rotary shaft 61 and has one edge 74a opening at a side edge of the drum 62. The processing spaces 74 are provided in association with the respective ultrasonic processing units 65a, 65b, 65c, 65d and, in each of the processing spaces 74, a horn 67 and an anvil 68 face each other (See FIG. 5). The respective ultrasonic processing units 65a through 65d are adapted to move forward (leftward as viewed in FIG. 4) and to move backward (rightward as viewed in FIG. 4) in the direction indicated by the two-headed arrow A as the respective carriers 66 slide on associated slide rails 77 in the column 75. In FIG. 4, the ultrasonic processing unit 65a is illustrated to lie in the backmost position and the ultrasonic processing unit 65c is illustrated to lie in the foremost position. The ultrasonic processing units 65b, 65d as illustrated in FIG. 3 lie in the intermediate positions between the forefront position and the backmost position. The respective ultrasonic processing units 65a through 65d reciprocate once between the backmost position and the forefront position for every rotation of the drum 62 in the direction RD. Details of the manner in which the ultrasonic processing units 65a through 65d reciprocate will be described with reference to FIG. 6.

Figure 5:
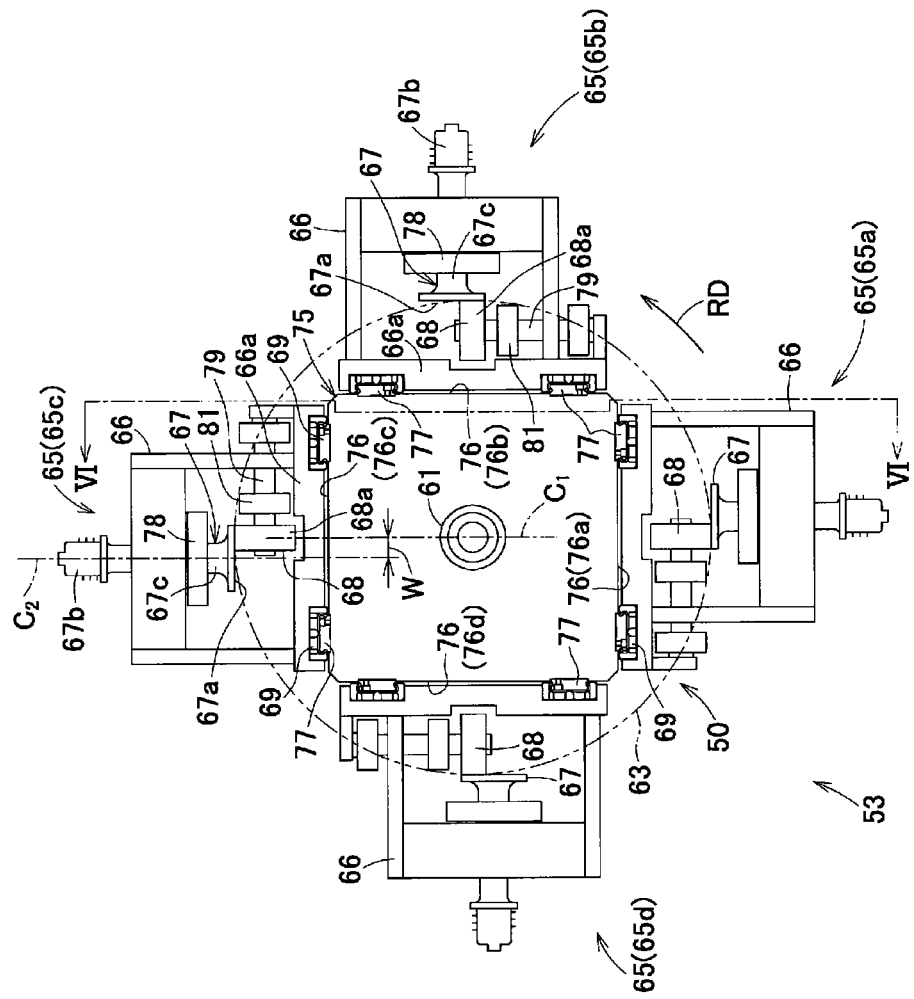
FIG. 5 A view similar to FIG. 3 with a drum dismounted.

Referring to FIG. 5, it is a view similar to FIG. 3 except that the drum 62 is illustrated to have been dismounted from the rotary shaft 61 and the outer peripheral surface 63 alone is indicated by an imaginary line. A cross-sectional shape of the column 75 lying inside the drum 62 viewed in the direction orthogonal to the rotary shaft 61 is substantially square and a peripheral surface 76 of the column 75 includes peripheral surface segments 76a, 76b, 76c, 76d facing the ultrasonic processing units 65a through 65d, respectively. Each of these peripheral surface segments 76a through 76d includes a pair of slide rails 77 extending in parallel to the rotary shaft 61. Each of the ultrasonic processing units 65a through 65d includes the carrier 66, the horn 67 and the anvil 68. Each of the carriers 66 moves back-and-forth in both directions A (See FIG. 6) as slide shoes 69 attached to a plate-like portion 66a slide on respective slide rails 77. The horn 67 has a disk-shaped working surface 67a facing a peripheral surface 68a of the anvil 68, a booster 67c being contiguous to the working surface 67a and a converter 67b electrically connected to the ultrasonic transmitting slip ring 73 (See FIG. 4), wherein an intermediate portion defined between the working surface 67a and the converter 67b is rotatably supported by the carrier 66. Assuming that the ultrasonic processing spaces are not present, the working surface 67a is positioned so as to overlap the peripheral surface 63 and ultrasonically oscillates in continuous or intermittent fashion in response to signals applied from the slip ring 73 during operation of the ultrasonic processing apparatus 50. The working surface 67a rotates as a first driving belt 78 revolves around the pulley (not shown) attached to the booster 67c. The anvil 68 is attached to a shaft 79 and rotates together with the shaft 79 under operation of a second driving belt 81. Coming just above each of the processing spaces 74 of the drum 62, the fibrous web 31 is caught between the working surface 67a of the horn 67 and the peripheral surface 68a of the anvil 68 and sandwiched therebetween in the thickness direction. The working surface 67a of the horn 67 cooperates with the peripheral surface 68a of the anvil 68 to ultrasonically process the fibrous web 31. As exemplarily illustrated on the basis of the ultrasonic processing unit 65c, a first center line $C_1$ passing through the center of the rotary shaft 61 in the diametrical direction substantially bisects the width of the peripheral surface 68a of the anvil 68 and a second center line $C_2$ passing through the center of the working surface 67a of the horn 67 and extending in parallel to the first center line $C_1$ is spaced from the first center line $C_1$ by a dimension W. The second center line $C_2$ corresponds to a rotational center of the horn 67. In FIG. 5, to avoid complexity of illustration, reference numerals for the ultrasonic processing units 65a, 65d are limited to the main portions thereof.

Figure 6:
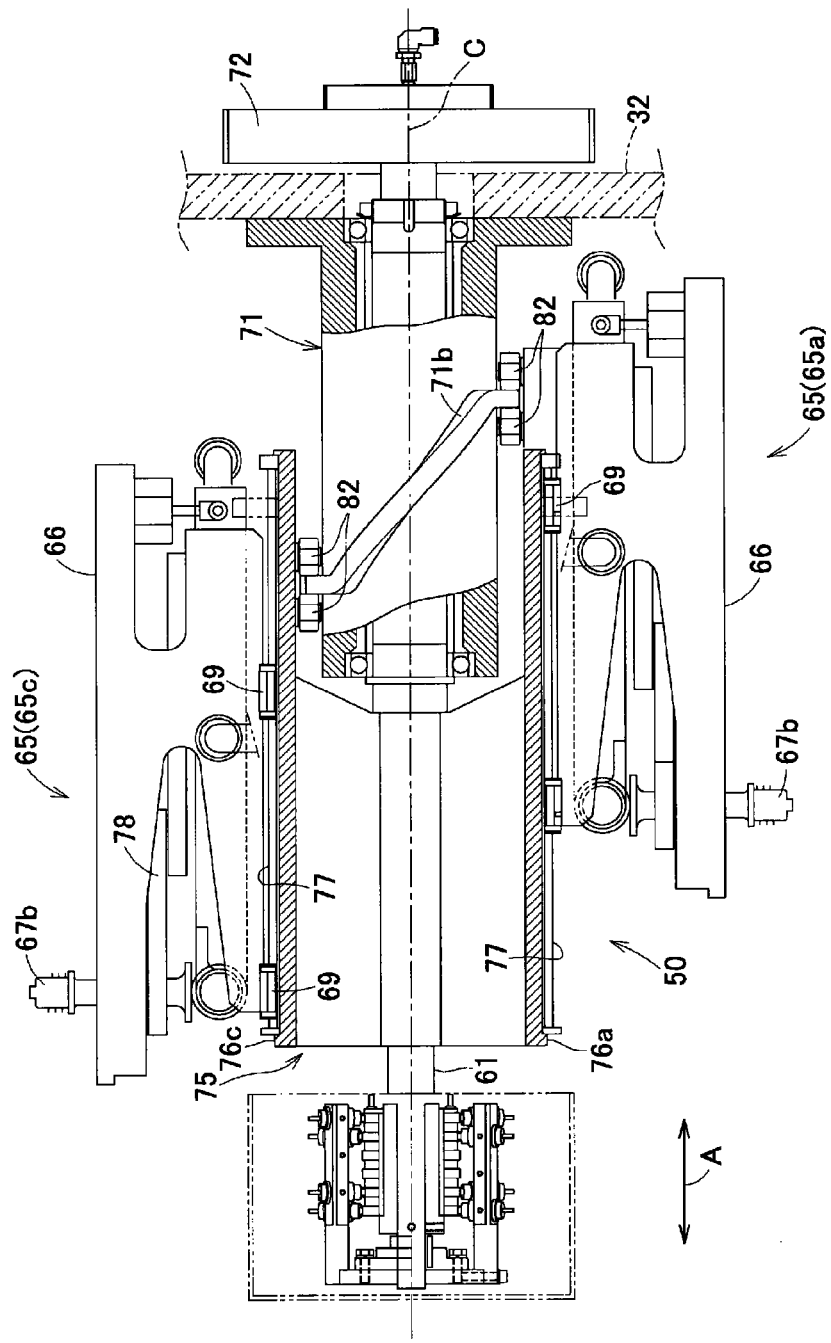
FIG. 6 A sectional view taken along line VI-VI in FIG. 5.

Referring to FIG. 6, this is a sectional view taken along line VI-VI in FIG. 5 wherein the drum 62 is not shown for convenience of illustration. The stationary cylinder 71 and the column 75 are illustrated in partially cutaway fashion. It should be appreciated that hatchings indicating the respective cross-sectional surfaces are partially eliminated to avoid complexity of illustration. The stationary cylinder 71 extending forward from the wall 32 is formed on its peripheral surface with the rib-like cam 71b so that the cam followers 82 in the respective carriers 66 associated with the ultrasonic processing units 65a through 65d may move along the cam 71b to move the respective carriers 66. The column 75 is fixed to the rotary shaft 61 which extends through the stationary cylinder 71 so that the column 75 may rotate together with the rotary shaft 61. The respective peripheral surface segments 76a through 76d of the column 75 are respectively formed with the slide rails 77 and the respective carriers 66 in the ultrasonic processing units 65a through 65d are placed on the associated slide rails 77 by means of the slide shoes 69. The carriers 66 are adapted to move back-and-forth in the both directions indicated by the two-headed arrow A along the slide rails 77 so that the carriers 66 should not come off the slide rails 77 in the course of rotation of the drum 62 together with the column 75 in the direction RD (See FIG. 5). When the rotary shaft 61 rotates in the direction indicated by the arrow RD in response to rotation of the main pulley 72 in the direction indicated by the arrow RD, the column 75 fixed to the rotary shaft 61 also rotates in the direction indicated by the arrow RD. The carriers 66 adapted to move back-and-forth relative to the column 75 repetitively move back-and-forth as the cam followers 82 attached to the respective carriers 66 move along the cam 71b. The forefront position and the backmost position for each of the back-and-forth moving carriers 66 are regulated by the cam 71b. Specifically, in response to one revolution of the column, the ultrasonic processing units, for example, the ultrasonic processing unit 65a in FIG. 6 rotates in the direction indicated by the arrow RD and, in the course of this one revolution, the ultrasonic processing unit 65a passes the positions of the ultrasonic processing units 65b, 65c, 65d in FIGS. 5 and 6 in this order and then returns to its position shown in FIG. 6.

Figure 7:
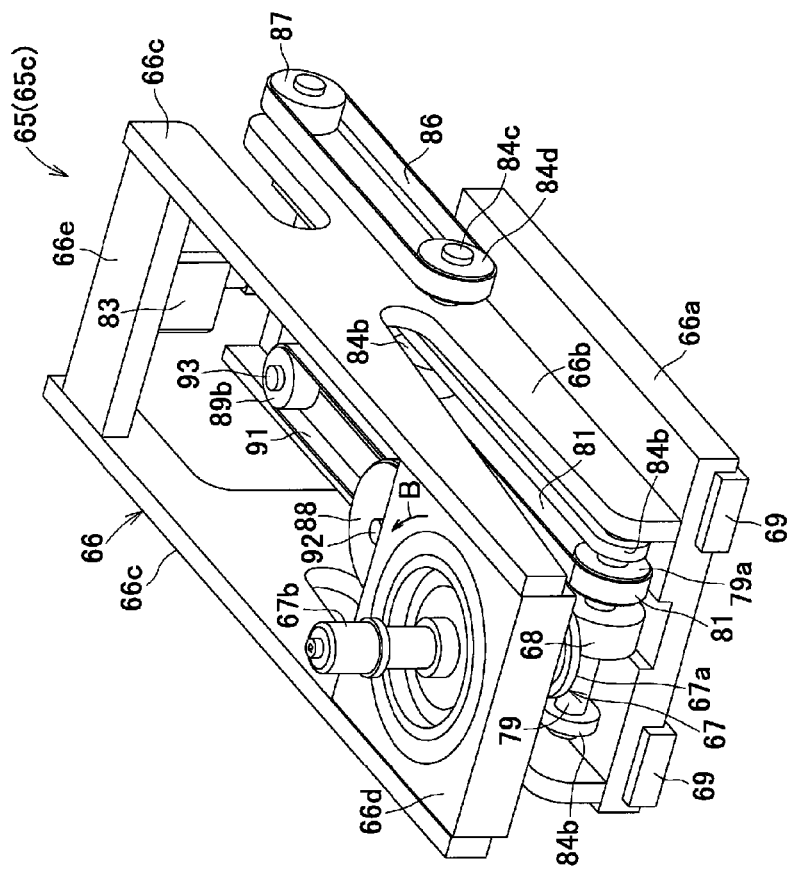
FIG. 7 A perspective view of ultrasonic processing elements.
Figure 8:
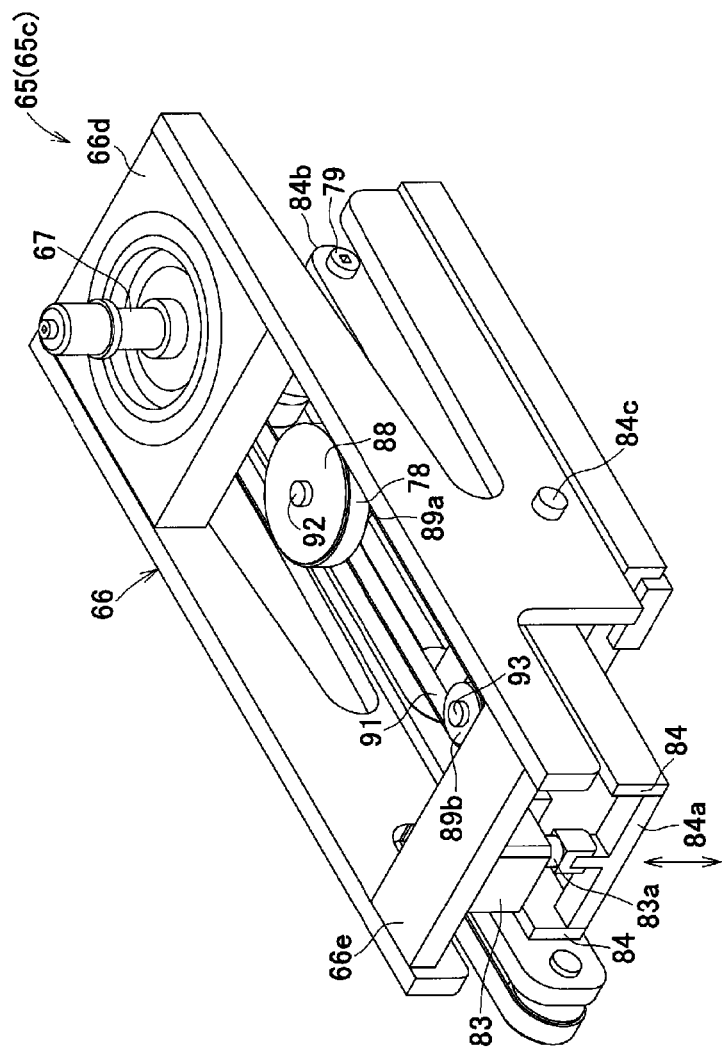
FIG. 8 A perspective view of ultrasonic processing elements.

Referring to FIGS. 7 and 8, these illustrate details of the ultrasonic processing units 65 exemplarily on the basis of the ultrasonic processing unit 65c shown in FIGS. 5 and 6 wherein FIG. 7 is a perspective view of the ultrasonic processing unit 65c as viewed from the front and FIG. 8 is a perspective view of the ultrasonic processing unit 65c as viewed from behind. The carriers 66 include a frame 66b placed above a plate 66a. The frame 66b includes a pair of lateral plates 66c, a front connector plate 66d and a rear connector plate 66e both serving to connect the lateral plates 66c to each other. The front connector plate 66d supports the horn 67 so that the horn 67 may rotate in the direction indicated by an arrow B and in the direction opposite thereto. The rear connector plate 66e has the air cylinder 83 attached thereto. A rod 83a extending downward from the air cylinder 83 is adapted to be supplied with compressed air from the rotary connector 72c cooperating with the main pulley 72 (See FIG. 4) and thereby to be moved up-and-down. A lower end of the rod 83a is connected to a bridge 84a serving to connect a pair of anvil pressurizing arms 84 to each other. The arms 84 are rotatably supported by a shaft 84c and the shaft 79 of the anvil 68 is rotatably inserted into front ends of the arms 84. In response to forward movement of the ultrasonic processing unit 65c, the rod 83a moves downward as viewed in FIG. 7 and the anvil 68 is moved upward by the arm 84 so as to come close to the horn 67. In this way, the portion of the fibrous web 31 lying between the horn 67 and the anvil 68 can be pressed against the working surface 67a of the horn 67. In response to backward movement of the ultrasonic processing unit 65c, the rod 83a moves upward while the anvil 68 moves downward and cooperation for the ultrasonic processing between the horn, which is continuously ultrasonically oscillating, and the anvil 68 can be put at a standstill. It is also possible to temporarily halt ultrasonic oscillations of the horn 67 in the course of backward movement of the ultrasonic processing unit 65c. Upon completion of backward movement of the ultrasonic processing unit 65c, the rod 83a moves again downward to restart the cooperation between the horn 67 and the anvil 68. A detecting means such as a limit switch (not shown) attached to the column 75 detects that the ultrasonic processing unit 65c has reached the forefront position and/or the backmost position and outputs a detection signal adapted to actuate the air cylinder 83.

The second driving belt 81 put around a pulley 79a fixed to the shaft 79 of the anvil 68 is also put around the pulleys 84b fixed to the shaft 84c. Front pulleys 84d are fixed on portions of the shaft 84c extending outward beyond the lateral plates 66b. Fixed belts 86 are put around the front pulleys 84d, respectively. These fixed belts 86 are also put around rear pulleys 87 rotatably attached to the rear ends of the lateral plates 66b, respectively. The fixed belts 86 lying outside the lateral plates 66b are fixed to column 75 in appropriate regions of the column 75 so that the front pulleys 84d and the rear pulleys 87 may be put in engagement with the fixed belts 86 and rotated. Thereupon the shaft 84c and the second driving belts 81 put around the shaft 84c can be rotated and the anvil also can be rotated. The anvil 68 rotates in the forward direction when the ultrasonic processing unit 65c moves forward and rotates in the backward direction when the anvil 68 moves backward.

The first driving belt 78 operatively associated with the horn 67 is put around a pulley 88 located behind the horn 67. A first fixed belt 91 is put around a first lower pulley 89a which is coaxial with and underlies the pulley 88 on the one hand, and put around a second lower pulley 89b located behind the first lower pulley 89a on the other hand. In response to back-and-forth movement of the ultrasonic processing unit 65c, the first lower pulley 89a and the second lower pulley 89b rotate in engagement with the first fixed belt 91, causing the pulley 88 and the first driving belt 78 to be rotated and the horn 67 also to be rotated. The horn 67 rotates in the direction indicated by the arrow B when the ultrasonic processing unit 65c moves forward and the horn 67 rotates in the opposite direction when the ultrasonic processing unit 65c moves backward. Though not illustrated, respective central shafts 92, 93 of the pulley 88 and the second lower pulley 89b are fixed to the carrier 66. The first fixed belt 91 is fixed to the column 75 in an appropriate region of the column 75.

Figure 9:
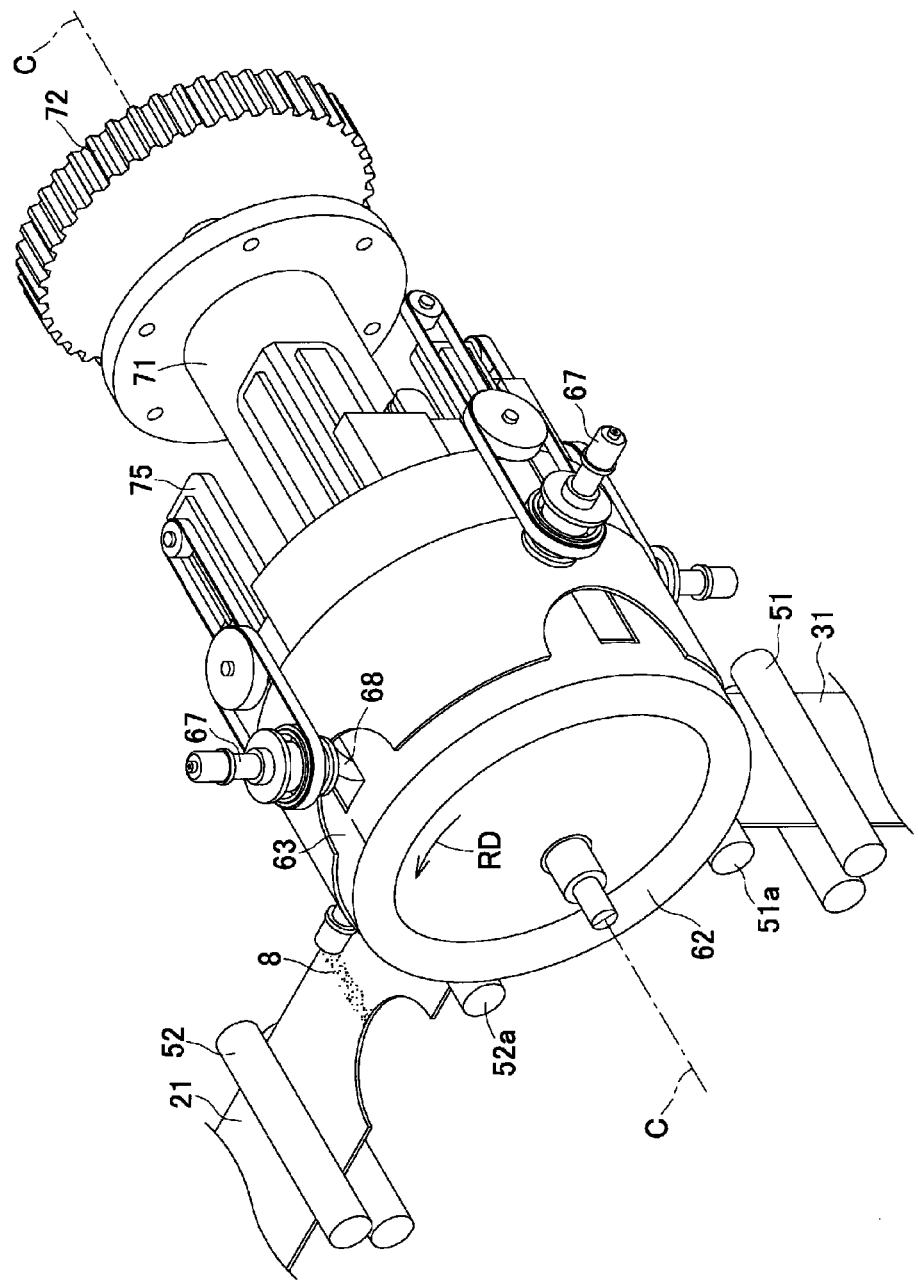
FIG. 9 A schematic diagram of the ultrasonic processing apparatus, illustrating flow of the fibrous web.

Referring to FIG. 9, this is a schematic perspective view of the ultrasonic processing apparatus 50 wherein the fibrous web 31 is put on the peripheral surface 63 of the drum 62 and the horn 67 cooperates with the anvil 68 to ultrasonically process the fibrous web 31. In FIG. 9, the members hiding the fibrous web 31 put on the drum 62 are not shown for convenience of illustration. The fibrous web 31 transported by the guide roll 51a onto the peripheral surface 63 of the drum 62 is subjected to ultrasonic processing started by the ultrasonic processing unit 65 lying at the position of the ultrasonic processing unit 65a in FIG. 3 and completed by the ultrasonic processing unit 65 lying at the position of the ultrasonic processing unit 65c in FIG. 3. In this way, the web of contiguous diapers 21 is formed from the fibrous web 31 and transported away from the ultrasonic processing apparatus 50 by the second guide roll 52 serving as the conveying means.

With regard to the ultrasonic processing apparatus 50 as has been described above, the horn 67 serving as the second mechanical elements cooperates with the anvil 68 serving as the first mechanical elements to ultrasonically process the fibrous web 31 running in the machine direction MD together with the drum 62. In the course of this processing, the working surface 67a of the horn 67 slides on the fibrous web 31 so as to pass transversely across the fibrous web 31. Therefore, even if a thermoplastic synthetic resin contained in the fibrous web 31 is molten by ultrasonic processing and the molten thermoplastic synthetic resin is partially transferred in the form of a small agglomerate from the fibrous web 31 onto the horn 67, such small agglomerate may be wiped off by the fibrous web 31 and the small agglomerate should not interfere with ultrasonic processing. With the horn 67 rotating in a manner that the working surface 67a thereof rubs the surface of the fibrous web 31 as in the illustrated embodiment, the small agglomerate of thermoplastic synthetic resin clinging to the working surface 67a of the horn 67 can be wiped off by the fibrous web 31. With the working surface 67a of the horn 67 rotating in this manner, a circumferential velocity of the horn 67 in its region facing the anvil 68 and a running velocity of the fibrous web 31 are preferably regulated so that a relative velocity of the working surface 67a and the fibrous web 31 may be appropriately differentiated in a range desirable for ultrasonic sealing of the fibrous web 31 and the working surface 67a and the fibrous web 31 may rub each other. To satisfy such requirement, it is preferred that the pulley 88, the first and second lower pulleys 89a, 89b (See FIGS. 7 and 8) can be easily exchanged with those having different diameters.

In the ultrasonic processing apparatus 50, the anvil 68 also rotates and rubs the fibrous web 31 as the anvil 68 passes transversely across the fibrous web 31. In this way, the small agglomerate of thermoplastic synthetic resin should not adhere to the anvil 68. The anvil 68 may be constructed in coolable or heatable type to prevent the small agglomerate of thermoplastic synthetic resin from adhering to the anvil 68. For example, it is possible to use the anvil 68 in the state heated at temperature in a range of 70 to 80° C. or higher or in the state cooled at temperature in a range of 0 to −5° C.

Figure 10:
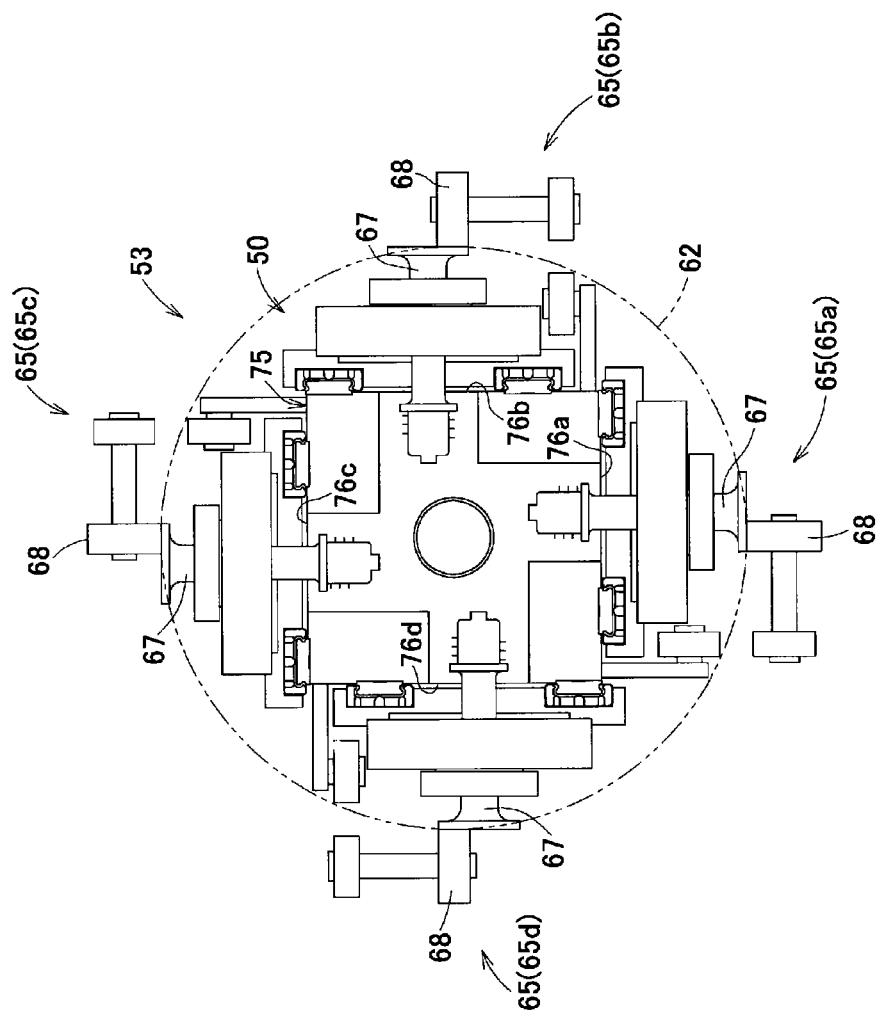
FIG. 10 A view similar to FIG. 5, showing one embodiment of the present invention.

Referring to FIG. 10, it is a view similar to FIG. 5, showing an embodiment of the ultrasonic processing apparatus 50. In the ultrasonic processing station 53 according to this embodiment, the first mechanical elements provided inside the drum 62 are four horns 67 and the second mechanical elements provided outside the drum 62 are four anvils 68 respectively facing the horns 67. The ultrasonic processing units 65a, 65b, 65c, 65d respectively including the horns 67 and the anvils 68 are attached to the peripheral surface segments 76a, 76b, 76c, 76d of the column 75, respectively, in a manner that these ultrasonic processing units may move back-and-forth in the longitudinal direction. While not shown in detail, this embodiment is constructed in a manner that the anvils 68 provided outside the drum 62 may come close to and spaced from the associated horns 67. In each of the ultrasonic processing units 65a through 65d, the anvil 68 comes close to the horn 67 as each of the ultrasonic processing units moves forward and thereby the anvil 68 cooperates with the horn 67 to process the fibrous web 31 ultrasonically.

While the second mechanical elements located outside the drum 62 are adapted to come close to and be spaced from the fibrous web 31 in the ultrasonic processing apparatus 50 having been exemplarily described, the effect of the present invention can be achieved with an arrangement such that at least one of the first and second mechanical elements is spaced from the fibrous web 31 when the ultrasonic processing of the fibrous web 31 by the ultrasonic processing apparatus 50 is temporarily stopped. The ultrasonic processing apparatus 50 is applicable, in addition to the ultrasonic seal processing of the fibrous web 31 as has been exemplarily described above, to other intended purposes, for example, partially cutting the fibrous web 31 and ultrasonic sealing the fibrous web 31 along an edge of the fibrous web 31 resulting from such partial cutting.

The first aspect described above may be arranged in at least the following features which are not limited to the detailed embodiments described above. The first aspect relates to the apparatus for repetitive ultrasonic processing of a fibrous web continuously running in a machine direction by first and second mechanical elements adapted to sandwich the fibrous web in its thickness direction.

The apparatus includes an upstream side conveying means and a downstream side conveying means adapted to run the fibrous web continuously in the machine direction.

A drum is located between the upstream side conveying means and the downstream side conveying means, the drum having an outer peripheral surface adapted to continuously rotate at a circumferential velocity equal to a running velocity of the fibrous web and adapted to support the fibrous web placed thereon, the outer peripheral surface being formed with at least one ultrasonic processing space being in communication with the inside and the outside of the drum.

The first mechanical elements are each located inside the drum in one of the processing spaces so that the first mechanical element is adapted to repetitively move back-and-forth in the direction crossing the machine direction and to pass transversely across the fibrous web.

The second mechanical elements are each located outside the drum in one of the processing spaces and adapted so that the second mechanical element may repetitively move back-and-forth in synchronization with the back-and-forth movement of the first mechanical element in the same direction as the direction in which the first mechanical element moves back-and-forth.

The first and second mechanical elements are adapted to cooperate with each other to subject the fibrous web lying in each of the processing spaces during one of the forward and backward movements to ultrasonic processing, and at least one of the first and second mechanical elements is adapted to be spaced from the fibrous web in order to stop the ultrasonic processing during the other of the forward and backward movements.

The first aspect may include at least the following embodiments.

(i) The first mechanical element is an ultrasonic horn and the second mechanical element is an anvil.

(ii) The first mechanical element is the anvil and the second mechanical element is the ultrasonic horn.

(iii) The ultrasonic horn has a working surface facing the anvil and the working surface is adapted to rotate around a shaft extending in parallel to a direction orthogonal to a central shaft of the drum in order to perform the ultrasonic processing.

(iv) A relative velocity between a portion of the working surface to be processed with ultrasonic waves and the fibrous web is adjustable.

(v) The anvil is formed by a roller adapted to rotate in the direction of the forward movement as well as in the direction of the backward movement.

(vi) The apparatus further includes:
 a column provided inside the drum and configured to rotate together with the drum,
 a stationary cylinder provided inside the column and configured to be kept stationary, the stationary cylinder being provided on its peripheral surface with a rib-like cam protruding from its peripheral surface, and
 a plurality of carriers configured to slide along a peripheral surface of the column, each of the carriers being provided with one of the first mechanical elements and corresponding one of the second elements, and each of the carriers being further provided with a cam follower which is configured to be moved along the rib-like cam of the stationary cylinder such that the carrier moves back and forth once relative to the column in response to one revolution of the drum.

(vii) Each of the carriers includes:
 a frame including a pair of lateral plates, a front connector plate and a rear connector plate both serving to connect the lateral plates to each other, the second mechanical element being supported on the front connector plate,
 an anvil pressurizing arm on one end of which the first mechanical element is supported,
 a cylinder attached to the rear connector plate,
 a rod extending downward from the cylinder and configured to drive another end of the anvil pressurizing arm to move up-and-down such that the first and the second mechanical elements move towards and away from each other.

The second aspect described above may be arranged in at least the following features which are not limited to the detailed embodiments described above. The second aspect relates to the method for repetitive ultrasonic processing of a fibrous web continuously running in a machine direction by first and second mechanical elements adapted to sandwich the fibrous web in its thickness direction.

The method includes the steps of continuously feeding the fibrous web in the machine direction and placing the fibrous web on an outer peripheral surface of a drum continuously rotating at a circumferential velocity equal to a running velocity of the fibrous web;

using the first mechanical elements, each located inside the drum in one of a plurality of ultrasonic processing spaces formed in the outer peripheral surface of the drum so as to be in communication with the inside and the outside of the drum, to repeat back-and-forth movement in a direction crossing the machine direction and to pass transversely across the fibrous web, and using the second mechanical elements each located outside the drum at the ultrasonic processing space to move back-and-forth in synchronization with the back-and-forth movement of the first mechanical element in the same direction as the direction in which the first mechanical element moves back-and-forth; and arranging the first and second mechanical elements to cooperate with each other during either the forward movement or the backward movement to subject the fibrous web lying in each of the processing spaces with the ultrasonic processing, and spacing at least one of the first and second mechanical elements from the fibrous web during the other of the forward movement and the backward movement to stop the ultrasonic processing.

The second aspect may include at least the following embodiments.

(i) The first mechanical element is an ultrasonic horn and the second mechanical element is an anvil.

(ii) The first mechanical element is the anvil and the second mechanical element is the ultrasonic horn.

(iii) The ultrasonic horn has a working surface facing the anvil and the working surface rotates around a shaft extending in parallel to a direction orthogonal to a central shaft of the drum to perform the ultrasonic processing.

(iv) A roller adapted to rotate in respective directions of the forward and backward movement is used as the anvil.

(v) A relative velocity between a portion of the working surface performing the ultrasonic processing and the fibrous web is adjustable.

In the apparatus of the present invention, the upstream conveying means preferably includes a pair of first guide rolls, and the downstream conveying means preferably includes a pair of second guide rolls.

An ultrasonic processing station is located between the first and second guide rolls, in one embodiment. This ultrasonic processing station includes a drum which is preferably adapted to rotate together with a rotary shaft.

In one embodiment, the ultrasonic processing station further includes four ultrasonic processing units which are arranged at regular intervals in a circumferential direction of the drum and are adapted to rotate together with the rotary shaft. These ultrasonic processing units are preferably provided separately of the drum; preferably between two and six ultrasonic processing units are provided.

In addition to the drum, the rotary shaft may be provided with a column lying inside the drum and fixed thereto so that the column may also rotate together with the rotary shaft.

The rotary shaft may extend through a stationary cylinder which may be provided on its peripheral surface with a rib-like cam protruding from its peripheral surface. The ultrasonic processing units, in this embodiment, are each provided with cam followers so that the ultrasonic processing units may move along the cam. This enables the ultrasonic processing units to move back and forth relative to the column. Moreover, in response to one revolution of the column, the ultrasonic processing units may each revolve once around the drum.

The outer peripheral surface of the drum is provided with a plurality of ultrasonic processing spaces which are preferably elongate. In one embodiment, each of the processing spaces extends in parallel to the rotary shaft and has one edge opening at a side edge of the drum. The processing spaces are provided in association with the respective ultrasonic processing units. Preferably, in each of the processing spaces, a horn and an anvil face each other. The respective ultrasonic processing units preferably reciprocate once between their backmost position and foremost position for every rotation of the drum in the direction of rotation (RD).

Preferably, the column lying inside the drum is substantially square in cross-section, particularly when four ultrasonic processing units are provided. However, if, for example, six ultrasonic processing units are provided, then the column lying inside the drum may be hexagonal in cross-section. In a preferred embodiment, the column has a peripheral surface in cross-section including a peripheral surface segment facing an ultrasonic processing unit.

Each of the ultrasonic processing units may include a carrier, a horn and an anvil. Each of the carriers is adapted to move the ultrasonic processing unit backwards and forwards. Each of the carriers may be provided with one or more of the cam followers such that the respective carrier associated with an ultrasonic processing unit may move along the cam to provide the desired backwards and forwards movement.

As mentioned above, the ultrasonic horn may have a working surface which is adapted to rotate. Preferably the horn rotates in a manner such that its working surface is able to rub the surface of the fibrous web undergoing ultrasonic processing. The anvil may also be adapted to rotate and preferably this permits the anvil to rub the fibrous web as the anvil passes transversely across the fibrous web.

Preferably, the anvil is heated to at least 70° C. or alternatively the anvil may be cooled to a temperature in a range of 0 to −5° C.

REFERENCE SIGNS LIST 1 diaper
2 front waist region
3 rear waist region
4 crotch region
6 side edge of front waist region
7 side edge of rear waist region
8 seal region
11 waist opening
12 leg opening
13 inner sheet
14 outer sheet
21 web of contiguous diapers
22 proposed cutting lines
31 fibrous web
50 ultrasonic processing apparatus
51 conveying means (first guide roll)
52 conveying means (second guide roll)
53 ultrasonic processing station
61 rotary shaft
62 drum
63 peripheral surface
65 ultrasonic processing unit
66 carrier
67 first mechanical element (horn)
67a working surface
68 second mechanical element (anvil)
69 slide shoes
71 stationary cylinder
72 pulley
73 slip ring
74 processing spaces
75 column
76 peripheral surface segments
77 slide rails
78 first driving belt
79 shaft
81 second driving belt
82 cam followers
83 air cylinders
83 rod
84 arms
86 fixed belts
88 pulley
89a first lower pulley
89b second lower pulley
91 first fixed belt
92,93 central shafts of pulley 88
C axis (center lines)
MD machine direction
RD direction of rotation

The invention claimed is:

1. An apparatus for repetitive ultrasonic processing of a fibrous web continuously running in a machine direction by first and second mechanical elements adapted to sandwich the fibrous web in its thickness direction, wherein the apparatus comprises:
    an upstream side conveying means and a downstream side conveying means adapted to continuously run the fibrous web in the machine direction;
    a drum located between the upstream side conveying means and the downstream side conveying means, the drum having an outer peripheral surface adapted to continuously rotate in one direction at a circumferential velocity equal to a running velocity of the fibrous web and adapted to support the fibrous web placed thereon, the outer peripheral surface being formed with at least one ultrasonic processing space being in communication with the inside and the outside of the drum;
    the first mechanical elements each being located inside the drum in one of the processing spaces so that the first mechanical element is adapted to repetitively move back-and-forth in a direction crossing the machine direction to pass transversely across the fibrous web;
    the second mechanical elements each being located outside the drum in one of the processing spaces and adapted so that the second mechanical element repetitively moves back-and-forth in synchronization with the back-and-forth movement of the first mechanical element in the same direction as the direction in which the first mechanical element moves back-and-forth; and
    the first and second mechanical elements being adapted to cooperate with each other to subject the fibrous web lying in each of the processing spaces during one of the forward and backward movements to ultrasonic processing, and at least one of the first and second mechanical elements is adapted to be spaced from the fibrous web in order to stop the ultrasonic processing during the other of the forward and backward movements.

2. The apparatus defined by claim 1, wherein the first mechanical element is an ultrasonic horn and the second mechanical element is an anvil.

3. The apparatus defined by claim 1, wherein the first mechanical element is the anvil and the second mechanical element is the ultrasonic horn.

4. The apparatus defined by claim 2, wherein the ultrasonic horn has a working surface facing the anvil and the working surface is adapted to rotate around a shaft extending in parallel to a direction orthogonal to a central shaft of the drum in order to perform the ultrasonic processing.

5. The apparatus defined by claim 4, wherein a relative velocity between a portion of the working surface performing the ultrasonic processing and the fibrous web is adjustable.

6. The apparatus defined by claim 2, wherein the anvil is formed by a roller adapted to rotate in the direction of the forward movement as well as in the direction of the backward movement.

7. The apparatus defined by claim 1, further comprising:
- a column provided inside the drum and configured to rotate together with the drum,
- a stationary cylinder provided inside the column and configured to be kept stationary, the stationary cylinder being provided on its peripheral surface with a rib-like cam protruding from its peripheral surface, and
- a plurality of carriers configured to slide along a peripheral surface of the column, each of the carriers being provided with one of the first mechanical elements and corresponding one of the second elements, and each of the carriers being further provided with a cam follower which is configured to be moved along the rib-like cam of the stationary cylinder such that the carrier moves back and forth once relative to the column in response to one revolution of the drum.

8. The apparatus defined by claim 7, wherein each of the carriers comprises:
- a frame including a pair of lateral plates, a front connector plate and a rear connector plate both serving to connect the lateral plates to each other, the second mechanical element being supported on the front connector plate,
- an anvil pressurizing arm on one end of which the first mechanical element is supported,
- a cylinder attached to the rear connector plate,
- a rod extending downward from the cylinder and configured to drive another end of the anvil pressurizing arm to move up-and-down such that the first and the second mechanical elements move towards and away from each other.

9. A method for repetitive ultrasonic processing of a fibrous web continuously running in a machine direction by first and second mechanical elements adapted to sandwich the fibrous web in its thickness direction, the method comprising the steps of:
- continuously feeding the fibrous web in the machine direction and placing the fibrous web on an outer peripheral surface of a drum continuously rotating in the machine direction at a circumferential velocity equal to a running velocity of the fibrous web;
- using a first mechanical element, located inside the drum in one of a plurality of ultrasonic processing spaces formed in the outer peripheral surface of the drum so as to be in communication with the inside and the outside of the drum, to repeat back-and-forth movement in a direction crossing the machine direction and to pass transversely across the fibrous web, and using a mechanical element located outside the drum in the ultrasonic processing space to move back-and-forth in synchronization with the back-and-forth movement of the first mechanical element in the same direction as the direction in which the first mechanical element moves back-and-forth; and
- arranging the first and second mechanical elements to cooperate with each other during either the forward movement or the backward movement to subject the fibrous web lying in each of the processing spaces to the ultrasonic processing, and spacing at least one of the first and second mechanical elements from the fibrous web during the other of the forward movement and the backward movement to stop the ultrasonic processing.

10. The method defined by claim 9, wherein the first mechanical element is an ultrasonic horn and the second mechanical element is an anvil.

11. The method defined by claim 9, wherein the first mechanical element is the anvil and the second mechanical element is the ultrasonic horn.

12. The method defined by claim 10, wherein the ultrasonic horn has a working surface facing the anvil and the working surface rotates around a shaft extending in parallel to a direction orthogonal to a central shaft of the drum to perform the ultrasonic processing.

13. The method defined by claim 10, wherein a roller adapted to rotate in respective directions of the forward and backward movement is used as the anvil.

14. The method defined by claim 12, wherein a relative velocity between a portion of the working surface performing the ultrasonic processing and the fibrous web is adjustable.

15. The method defined by claim 13, wherein a relative velocity between a portion of the working surface performing the ultrasonic processing and the fibrous web is adjustable.

16. The apparatus defined by claim 3, wherein the ultrasonic horn has a working surface facing the anvil and the working surface is adapted to rotate around a shaft extending in parallel to a direction orthogonal to a central shaft of the drum in order to perform the ultrasonic processing.

17. The apparatus defined by claim 16, wherein a relative velocity between a portion of the working surface performing the ultrasonic processing and the fibrous web is adjustable.

18. The apparatus defined by claim 3, wherein the anvil is formed by a roller adapted to rotate in the direction of the forward movement as well as in the direction of the backward movement.

19. The apparatus defined by claim 4, wherein the anvil is formed by a roller adapted to rotate in the direction of the forward movement as well as in the direction of the backward movement.

20. The method defined by claim 11, wherein the ultrasonic horn has a working surface facing the anvil and the working surface rotates around a shaft extending in parallel to a direction orthogonal to a central shaft of the drum to perform the ultrasonic processing.

* * * * *